United States Patent [19]

Malcolm et al.

[11] Patent Number: 4,655,763

[45] Date of Patent: Apr. 7, 1987

[54] TESTING AND DISPENSING APPARATUS FOR AN ENTERAL FEEDING SYSTEM

[75] Inventors: ALexander R. Malcolm, Dudley; David M. Gessner, Worcester, both of Mass.

[73] Assignee: Nutrapack, Inc., Worcester, Mass.

[21] Appl. No.: 605,584

[22] Filed: Apr. 30, 1984

[51] Int. Cl.$^{4}$ .......................... A61J 3/00; A61M 5/00

[52] U.S. Cl. .................................... 604/404; 604/411; 436/200; 436/163

[58] Field of Search ................ 436/163, 200; 422/101, 422/134, 223; 604/23, 99, 195, 280, 411, 404

[56] References Cited

U.S. PATENT DOCUMENTS

| | | | |
|---|---|---|---|
| 1,615,873 | 2/1927 | Fitch | 604/411 |
| 2,409,343 | 10/1946 | Curtis | 604/411 |
| 2,626,855 | 1/1953 | Hand | 436/163 |
| 2,671,028 | 3/1954 | Clark | 435/189 |
| 2,817,372 | 12/1957 | Barr, Sr. et al. | 604/411 |
| 3,067,015 | 12/1962 | Lawdermilt | 422/56 |
| 3,346,464 | 10/1967 | Ernst | 435/31 |
| 3,373,735 | 3/1968 | Gallagher | 604/280 |
| 4,058,121 | 11/1977 | Choski et al. | 604/411 |
| 4,282,863 | 8/1981 | Beigler et al. | 128/1 R |
| 4,473,094 | 9/1984 | Harris | 604/411 |

*Primary Examiner*—S. Leon Bashore
*Assistant Examiner*—Michael K. Boyer
*Attorney, Agent, or Firm*—Ralph W. Selitto, Jr.

[57] ABSTRACT

A sterile testing and dispensing apparatus is adapted for insertion into a sterile aseptically packaged container to permit the contents of the container to be tested and then dispensed. The apparatus includes a dispensing tube and a pH indicator removably received in the dispensing tube. When inserting the dispensing tube into the container through an appropriate hole or weakened area therein, the pH indicator is automatically exposed to the contents of the container. The pH indicator can then be withdrawn from the dispensing tube and visually examined to determine the presence or absence or spoilage.

7 Claims, 4 Drawing Figures

TESTING AND DISPENSING APPARATUS FOR AN ENTERAL FEEDING SYSTEMcl FIELD OF THE INVENTION

The present invention relates to a testing and dispensing apparatus and method, and, more particularly, to such an apparatus and method which are especially adapted for use in connection with an enteral feeding system.

BACKGROUND OF THE INVENTION

Existing enteral nutritionals are supplied either as powders requiring mixing or as liquids contained in cans and bottles which require transfer to a secondary application container. The use of sterile aseptic packaging would allow these products to be supplied in a "ready to use" form. Furthermore, if the contents of these containers could be accessed in an aseptic manner, the contents would have a reduced susceptibility to spoilage during use and would require no refrigeration.

There are two separate and distinct problems which would normally prevent such aseptic access. The first problem is that the contents of the container could not be withdrawn without creating a partial vacuum in the container, unless the container were vented to the atmosphere. Because open venting would allow microbial invasion of the container, spoilage would result.

The other problem is that all low acid food processing is subject to a failure rate of about eight containers per one hundred thousand for microbiological reasons. Approximately five of these failures are due to bacteria which produce carbon dioxide that causes the container to swell and leak. Such failures are immediately apparent to any end user and would result in the container being discarded prior to use. However, the other three failures would be of the "flat sour" type. The bacteria which cause "flat sour" failures contaminate the contents of the container, but do not generate carbon dioxide. Thus, the spoilage is not readily apparent. The three characteristics associated with "flat sour" failures are off odors, curdling and increased acidity (the pH would be lowered from approximately 6.5 to about 4.8). Because feeding of such a spoiled product to a compromised patient might have catastrophic effects, all containers would normally be opened and then examined both visually and aromatically prior to use. Such inspection would prevent the nutritional from being transferred to the patient directly from the container.

In the past, pH indicators have been proposed for determining whether various types of food have spoiled (see, for instance, U.S. Pat. Nos. 2,626,855 and 3,067,015). However, none of these indicators is combined with an insertable dispensing device for dispensing the food after a determination has been made that the food is suitable for consumption.

Vented dispensing devices have also been proposed in the past (see, for instance, U.S. Pat. Nos. 1,615,873 and 2,409,343). However, none of these devices incorporates a spoilage indicator.

SUMMARY OF THE PRESENT INVENTION

The present invention relates to the testing and dispensing of the contents of a container, such as a low acid liquid nutritional contained in an aseptically packaged container, using a unique testing and dispensing apparatus which includes dispensing means for dispensing the contents of the container and indicating means for indicating the condition of the contents of the container. The indicating means is removably associated with the dispensing means so that the indicating means can be inserted into the container together with the dispensing means and then withdrawn from the container by removing the indicating means from the dispensing means. After the indicating means has been removed from the dispensing means, the indicating means can be visually inspected to determine the condition of the contents of the container before dispensing the contents from the container.

If, for instance, the testing and dispensing apparatus is used in connection with an enteral feeding system, the indicating means can be a pH indicator which provides a visual indication as to whether the acidity of a low acid food (i.e., a liquid nutritional) is in a range which would indicate that the food has spoiled. When the testing and dispensing apparatus is used in connection with such a system, the dispensing means is provided with venting means for venting the interior of the container to the outside atmosphere, whereby the creation of a partial vacuum in the container is inhibited during the withdrawal of the contents thereof. By providing the venting means with filtering means for filtering air flowing from the outside atmosphere to the interior of the container through the venting means, microbial contamination of the contents of the container can be inhibited. The dispensing means is also provided with puncturing means for puncturing the container to gain access to the interior thereof and covering means for covering the puncture formed in the container by the puncturing means.

In one embodiment, the dispensing means is a tubular element having a bore extending axially therethrough and the indicating means is an elongate member slidably received in the bore of the tubular element. More particularly, the tubular element includes a first end having a pointed tip adapted to puncture a container in order to gain access to the interior thereof and a second end having a connector adapted to connect the tubular element to a liquid distribution system. The elongate member includes a first end having a pH indicator positioned in the first end of the tubular element such that the pH indicator can be exposed to the contents of the container when the tubular element and the elongate member are inserted into the container as a unit. A second end of the elongate member extends outwardly from the second end of the tubular element and has a gripping handle adapted to be gripped by an individual to remove the elongate member from the bore of the tubular element. By removing the elongate member from the tubular element, the pH indicator can be viewed to provide a visual indication of the pH of the contents of the container.

BRIEF DESCRIPTION OF THE DRAWINGS

For a more complete understanding of the present invention, reference is made to the following detailed description of an exemplary embodiment considered in conjunction with the accompanying drawings, in which.

DESCRIPTION OF THE EXEMPLARY EMBODIMENT

Figure 1:
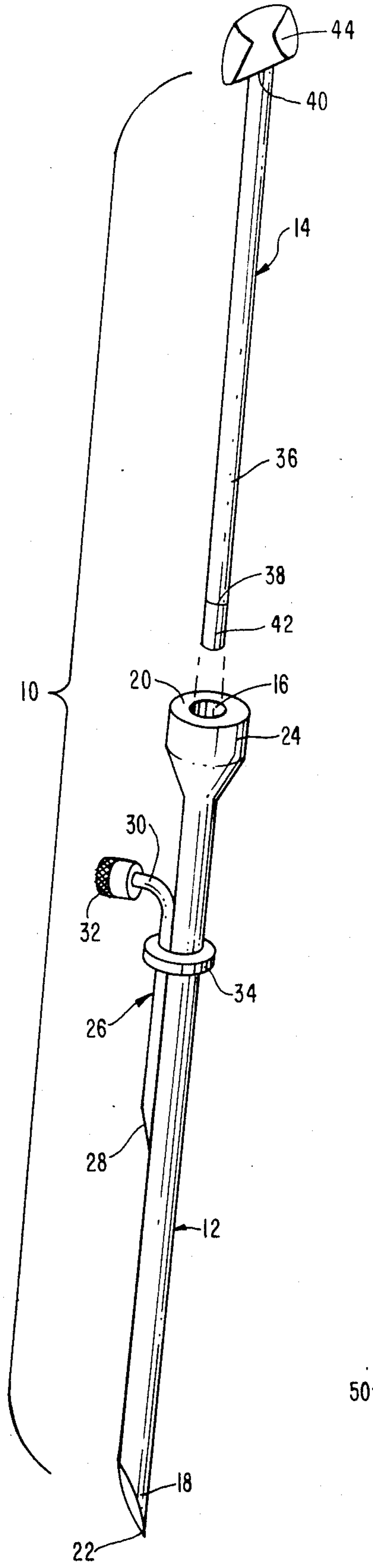
FIG. 1 is an exploded perspective view of a testing and dispensing apparatus constructed in accordance with the present invention and including a dispensing member and an indicating member adapted to be removably received in the dispensing member.
Figure 2:
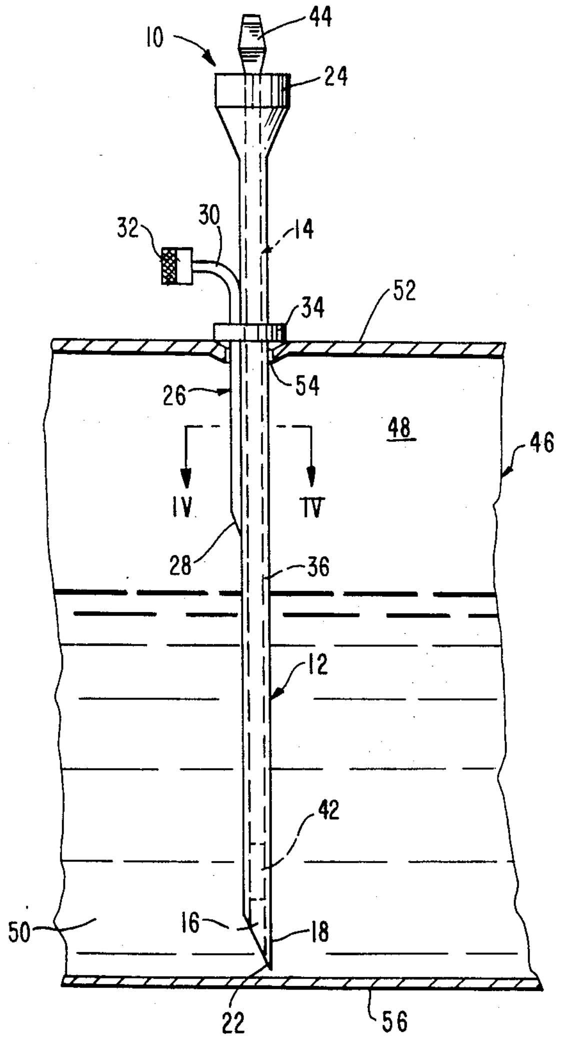
FIG. 2 is a cross-sectional view taken through a portion of an aseptically packaged container into which the testing and dispensing apparatus of FIG. 1 has been inserted with the indicating member removably received in the dispensing member.
Figure 3:
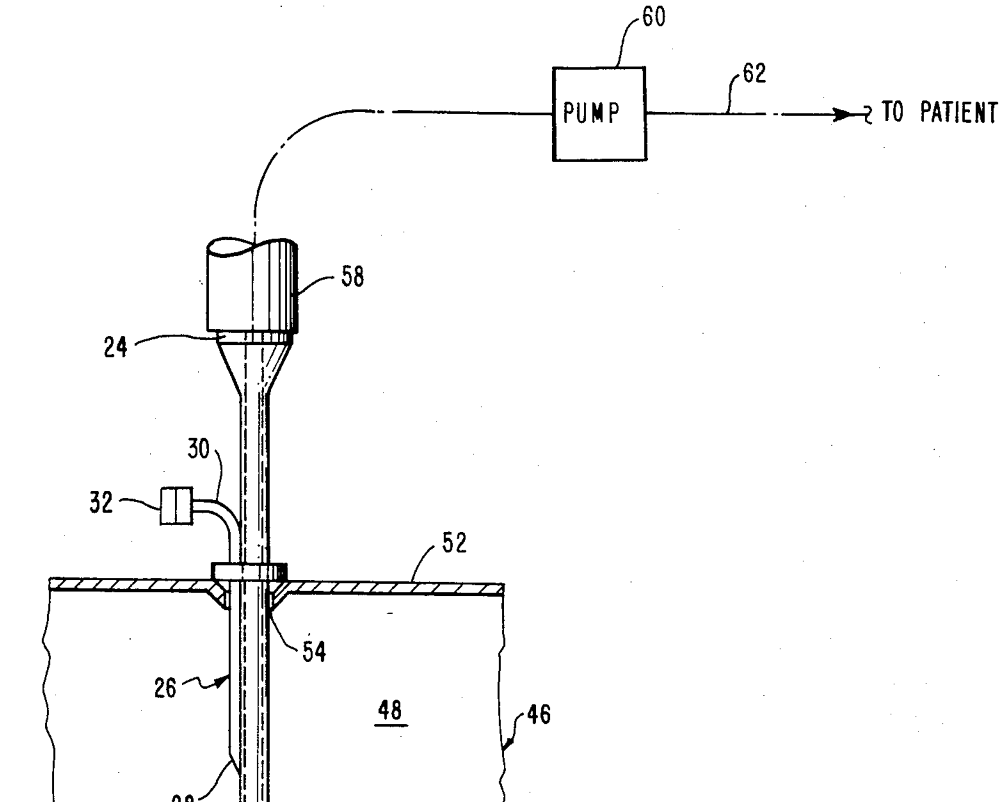
FIG. 3 is a view similar to FIG. 2, except that the indicating member has been removed from the dispensing member and the dispensing member has been connected to a liquid distribution system.
Figure 3:
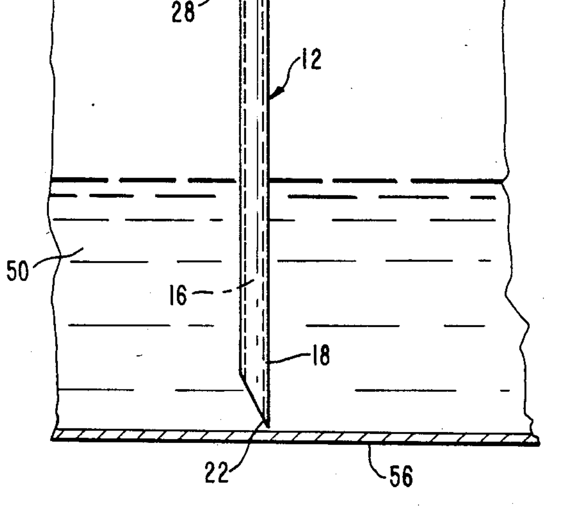

Although the present invention is applicable to many different types of liquid distribution systems, it is especially suitable for use in connection with an enteral feeding system. Accordingly, the present invention will be described in connection with an enteral feeding system.

Referring to FIGS. 1-4, a testing and dispensing apparatus 10 includes a food tube 12 and an indicating member 14. The food tube 12 is provided with a bore 16, which extends axially through the food tube 12 from a lower end 18 to an upper end 20. The lower end 18 of the food tube 12 terminates in a point 22. A connector 24 is provided at the upper end 20 of the food tube 12. A hollow vent tube 26 extends alongside the food tube 12. The vent tube has a pointed lower end 28 and a curved upper end 30, which receives a bacteriostatic filter cap 32 made from a porous material which is impervious to bacteria. A flange 34 extends around the food tube 12 and the vent tube 26. Except for the filter cap 32, the entire food tube is preferably made from plastic, although any other suitable material or materials may be used.

The indicating member 14 includes an elongate body 36, which is made from wood, plastic, rolled paper or any other suitable material and has a lower end 38 and an upper end 40. The lower end 38 of the body 36 terminates in a pH indicator 42 made from an absorbent material, such as paper or cotton, which has been chemically treated with a pH indicating substance adapted to change color depending upon the acidity of a liquid to which the pH indicator 42 is exposed. The upper end 40 of the body 36 is attached to a handle 44, which is made from any suitable material and has a size and shape selected so as to permit the handle 44 to be easily gripped by the fingers of an individual.

Figure 4:
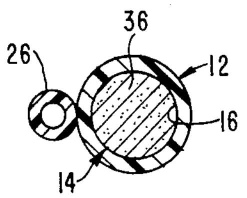
FIG. 4 is a cross-sectional view, taken along line IV—IV of FIG. 2 and looking in the direction of the arrows, of the testing and dispensing apparatus illustrated in FIG. 2.

The body 36 of the indicating member 14 has a circular cross-sectional shape (see FIG. 4) which substantially matches the circular cross-sectional shape of the bore 16 of the food tube 12 (see FIG. 4). Moreover, the diameter of the body 36 of the indicating member 14 is slightly less than the diameter of the bore 16 of the food tube 12 so that the body 36 of the indicating member 14 can be slidably and removably received within the bore 16 of the food tube 12. When the body 36 of the indicating member 14 is completely inserted into the bore 16 of the food tube 12, the pH indicator 42 is positioned in the lower end 18 of the food tube 12, while the gripping handle 44 of the indicating member 14 is positioned above the upper end 20 of the food tube 12.

In use in connection with an enteral feeding system, the testing and dispensing apparatus 10 would be removed from a suitable sterilized package and then inserted into an aseptically packaged container 46 whose interior 48 contains a low acid liquid nutritional 50. More particularly and with reference to FIG. 2, the food tube 12 and the indicating member 14 are inserted as a unit through a top wall 52 of the container 46 or through a metallic foil seal (not shown) in the top wall 52, the point 22 of the food tube 12 functioning to puncture the top wall 52 or the seal (not shown) as the testing and dispensing apparatus 10 is inserted into the container 46. The flange 34 limits the extent to which the testing and dispensing apparatus 10 is inserted into the container 46 and covers a puncture 54 formed in the top wall 52 of the container 46 by the point 22 of the food tube 12. When the flange 34 engages the top wall 52 of the container 46, the lower end 18 of the food tube 12 is in close proximity to a bottom wall 56 of the container 46. With the testing and dispensing apparatus 10 so positioned, the pH indicator 42 of the indicating member 14 is exposed to the liquid nutritional 50 contained in the interior 48 of the container 46.

In order to test the condition of the liquid nutritional 50, the indicating member 14 is removed from the food tube 12 by gripping the handle 44 of the indicating member 14 and sliding the body 36 of the indicating member 14 out of the bore 16 in the food tube 12. The pH indicator 42 of the indicating member 14 can then be visually examined to determine whether the acidity of the liquid nutritional 50 is in a range which would indicate that the liquid nutritional 50 has spoiled. For instance, if the pH indicator 42 has been treated with propyl red, a yellow color would indicate a pH of about 6.6 and hence that the liquid nutritional 50 has not spoiled and therefore is safe for consumption, while a red color would indicate a pH of about 4.8 and hence that the liquid nutritional 50 has spoiled and therefore is not safe for consumption.

If the liquid nutritional 50 is safe for consumption, the food tube 12 can be connected to a suitable liquid distribution system. More particularly and with reference to FIG. 3, a plastic conduit 58 is attached to the connector 24 on the upper end 20 of the food tube 12. The conduit 58 is also connected to an inlet (not shown) of a pump 60 (shown schematically). The pump 60 has an outlet (not shown), which is connected by a conduit 62 to a patient (not shown) to be supplied with the liquid nutritional 50 from the container 46.

As the liquid nutritional 50 is pumped from the container 46 to the patient (not shown), air from the outside atmosphere flows into the interior 48 of the container 46 through the vent tube 26 of the food tube 12, thereby inhibiting the creation of a partial vacuum in the container 46. The air flowing from the outside atmosphere to the interior 48 of the container 46 through the vent tube 26 passes through the filter cap 32 to thereby inhibit microbial contamination of the liquid nutritional 50 in the container 46.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

We claim:

1. An enteral feeding system, comprising an aseptically packaged container of a low acid liquid nutritional, a testing and dispensing apparatus including dispensing means for dispensing the liquid nutritional from the container, said dispensing means being a tubular element defining a bore extending axially therethrough, said tubular element including a first end having a pointed tip to puncture the container in order to gain access to the interior thereof and a second end having a connector, and indicating means for indicating the pH of the liquid nutritional and hence whether the liquid nutritional has spoiled, said indicating means being an elongate member which is slidably received in said bore of said tubular element such that said elongate member is removably associated with said tubular element, whereby said elongate member can be inserted into the container together with said tubular element and then withdrawn from the container by removing said elongate member from said tubular member, said elongate member including a first end having a pH indicator positioned in said first end of said tubular element, whereby said pH indicator may be exposed to the contents of the container when said tubular element and said elongate member are inserted into the container as a unit, and a second end extending outwardly from said second end of said tubular element and having a gripping handle to remove said elongate member from said bore of said tubular element, whereby said pH indicator can be viewed to provide a visual indication of the pH of the liquid nutritional and hence whether the liquid nutritional has spoiled, and withdrawing means connected to said connector of said tubular element for withdrawing the liquid nutritional from the container through said tubular element after said elongate member has been removed from said tubular element to provide a visual indication as to whether the liquid nutritional has spoiled.

2. An enteral feeding system according to claim 1, wherein said tubular element includes venting means for venting the interior of the container to the outside atmosphere, whereby the creation of a partial vacuum in the container is inhibited during the withdrawal of the liquid nutritional therefrom.

3. An enteral feeding system according to claim 2, wherein said venting means includes filtering means for filtering air flowing fron the outside atmosphere to the interior of the container through said venting means, whereby microbial contamination of the liquid nutritional in the container is inhibited.

4. An enteral feeding system according to claim 3, wherein said tubular element includes covering means for covering the puncture formed in the container by said pointed tip of said tubular element.

5. An enteral feeding system according to claim 4, wherein said covering means is a flange extending outwardly from said tubular element intermediate said first and second ends thereof.

6. An enteral feeding system according to claim 5, wherein said withdrawing means includes a pump connected between said tubular element and a patient.

7. An enteral feeding system according to claim 5, wherein said venting means includes a hollow vent tube extending alongside said tubular element and passing through said flange.

* * * * *